United States Patent [19]

Moroni

[11] Patent Number: 4,613,602

[45] Date of Patent: Sep. 23, 1986

[54] RANITIDINE DERIVATIVE USEFUL IN THE TREATMENT OF ULCER

[75] Inventor: Adolfo Moroni, Brescia, Italy

[73] Assignee: Magis Farmaceutici s.r.l., Brescia, Italy

[21] Appl. No.: 739,992

[22] Filed: May 31, 1985

[30] Foreign Application Priority Data

Jun. 12, 1984 [IT] Italy ................................ 21358 A/84

[51] Int. Cl.[4] .................. A61K 31/495; C07D 405/12
[52] U.S. Cl. ..................................... 514/252; 544/379
[58] Field of Search ......................... 544/379; 514/252

[56] References Cited

U.S. PATENT DOCUMENTS 3,505,338  4/1970  Blythe ................................. 544/379
4,123,529  10/1978  Verge et al. ......................... 544/379

*Primary Examiner*—Glennon H. Hollrah
*Assistant Examiner*—James H. Turnipseed
*Attorney, Agent, or Firm*—Stevens, Davis, Miller & Mosher

[57] ABSTRACT

As a structural modification of the molecule of ranitidine, its 1-(4-methyl-piperazinyl) derivative has been synthesized.

The product has shown to be active on the gastric secretion induced by histamine and on gastric and duodenal ulcers.

10 Claims, No Drawings

RANITIDINE DERIVATIVE USEFUL IN THE TREATMENT OF ULCER

The discovery of $H_2$—antagonists, drugs which inhibit the gastric secretion to a notable extent, through the blocking of histamine $H_2$—receptors, has received during these last years a great deal of attention.

This is due both to the confirmation of the existence of a receptor for the histamine, which was till then hypothetical only, and to the results actually obtained in the medical therapy of ulcer.

The pharmacological family of $H_2$—antagonists is not only important, but also prolific.

In fact, on considering the decade from 1972 to 1982, about ten potentially interesting $H_2$—antagonists have been identified among about a thousand compounds synthesized ad hoc by the industry.

General peculiar characteristic common to all $H_2$—antagonists is the intense blocking action on the gastric secretion bound to the competitive blocking of histamine $H_2$—receptors.

Anti-$H_2$ are presently the best weapon in the treatment of duodenal and gastric ulcer.

$H_2$ antagonism is of course accomplished to different degrees of power and selectivity for the different compounds.

Among the substances provided with $H_2$—receptor antagonist activity, a prominent position is occupied by ranitidine $$(CH_3)_2NCH_2\text{-furan-}CH_2SCH_2CH_2NHC(=CHNO_2)NHCH_3$$

Within our researches on the gastric secretion inhibiting drugs, it has been surprisingly found that the new compound synthesized by us having the formula:

$$\text{(I)} \quad (CH_3)_2N-H_2C\text{-furan-}CH_2-S-CH_2-CH_2NH-C(=CHNO_2)-N(\text{piperazino})N-CH_3$$

1-N—[2-[[5-[(dimethylamino)-methyl]-furfuryl]-thio]-ethyl]-amino-1-[4-methyl-piperazino]-2-nitro-ethene, and its pharmaceutically acceptable salts, are provided with an interesting activity of inhibition of gastric secretion. A reason for interest, of eminently pharmacological character, has resulted their therapeutical activity, practically overlapping to that of ranitidine.

On the basis of available data it can also be said that the side effects observed with this derivative are rather rare.

The new compounds and the salts thereof are characterized by a high activity, by a long lasting action and by a great safety, in that they are free from undesired effects and have a very low toxicity.

Their pharmaceutically acceptable salts comprise, e.g. both non toxic salts obtained by means of the addition of inorganic acids, such as e.g. hydrochloric, hydrobromic, hydriodic, phosphoric or sulphuric acid, and non toxic salts obtained by means of the addition of organic acids such as e.g. maleic, acetic, citric, oxalic, succinic, benzoic, tartaric, fumaric, mandelic, ascorbic, methylsulphonic or ethylsulphonic acid.

A further object of the present invention is a new process for the preparation of the compound of formula (I), as it has hereinabove defined, and of its pharmaceutically acceptable salts, characterized in that the compound of formula (III)

$$\text{(III)} \quad (CH_3)_2N-H_2C\text{-furan-}CH_2-S-CH_2-CH_2-S-CH_3$$

is reacted with the compound of formula (II)

$$\text{(II)} \quad NH_2-C(=CHNO_2)-N(\text{piperazino})N-CH_3$$

at the temperature of 80° C., the compound obtained is isolated and is optionally salified.

The characteristics of high activity and of practical absence of side effects have been evaluated by studying the acute toxicity, the activity on indomethacin-induced ulcers, on gastric secretion, on histamine-induced gastric hyperacidity, and on $H_2$—receptors of isolated uterus of guinea pig.

The acute toxicity has been studied on male and female mice of Swiss strain, and on albino male and female rats of Wistar strain, by administering the active principle by the oral way, by intravenous way, and by intramuscular way.

For each administering way envisaged, doses in geometrical progression have been tested.

At the end of the observation time period of 14 days, the $LD_{50}$ and the related fiducial limits have been computated according to the method by Licthfield and Wilcoxon [Pharmacol. Exp. Theor., 118, 96–99 (1949)].

The results are collected in Table 1.

TABLE 1

| $DL_{50}$ (95 fiducial limits) mg/kg | Mouse | | | Rat | | |
|---|---|---|---|---|---|---|
| | Oral admin istering | Intravenous administer- ing | Intramuscu- lar admin- istering | Oral admin istering | Intravenous administer- ing | Intramuscu- lar admin- istering |
| Ranitidine | 1700 (1246–2317) | 80 | 280 | >5000 | 93 | 2018 |
| Methylpiperazino- ranitidine | 2610 (1983–3435) | 120 | 300 | 5500 | 110 | 2000 |

From the whole of the data reported in the table, it is observed how methylpiperazino-ranitidine constantly results less toxic than ranitidine used to comparative purposes.

Study of Anti-Ulcer Activity

This activity has been evaluated by using the method of indomethacin-induced ulcers in rat [Bhargava, K. P., Gupta M. B. and Tangri, K. K.: European J. of Pharmacology, 22, 191–195 (1973)].

The results obtained are the following:

| Treatment | Dose, mg/kg p.o. | mm of ulcer | Inhibition percentage |
|---|---|---|---|
| Control | = | 18.4 | = |
| Ranitidine | 25 | 2.9 | 84.2 |
| Methylpiperazino-ranitidine | 25 | 2.6 | 85.9 |

The product has been administered as dissolved in carboxymethylcellulose at 0.2% and Tween 80 at 1% concentration.

From the data reported in table 1, methylpiperazino-ranitidine results to have the same anti-ulcer activity as ranitidine used to comparison purposes.

Study of Secretion-Inhibiting Activity

Anti-$H_2$ activity. Gastric secretion in rats in vivo induced by histamine.

The anti-secretory activity has been studied by the method by Gosh, M. N., Schild, M. O. [Brit. J. Pharmacol., 13, 54 (1958)].

The results are reported in the following Table 2. It can be observed that the compound according to the invention has an action prolonged in time: it can be noted indeed that from the 35th to the 60th minute the pH value remains nearly constant.

Antagonism to Histamine in Isolated Uterus of Female Rat Under Estrus

This activity has been evaluated by using the method by J. W. Black et al. [Nature, 236, 385–390 (1972)]. The results of the specific activity on $H_2$—receptors are reported in the following Table:

| Treatment | Concentration $10^{-3}$ g/l | N° | Relaxation with histamine $10^{-2}$ g/l | | | Inhibition percentage |
|---|---|---|---|---|---|---|
| | | | Basal value | After the administration | Δ | |
| Methylpiperazino-ranitidine | 6.75 | 5 | 11.5 | 2.5 | 9 | 78.2 |
| Ranitidine | 5 | 5 | 11.5 | 3 | 8.5 | 73.9 |

In this experiment too the activity of methylpiperazino-ranitidine is similar to that of ranitidine used as comparison.

Thanks to its characteristics of high activity and of practical absence of side effects, the compound of formula (I) and its pharmaceutically acceptable salts are particularly useful as the active principle in the formulation of pharmaceutical compositions; therefore, a further object of the present invention are the pharmaceutical compositions characterized in that they contain as their active principle an efficacious amount of the compound of formula (I) or of pharmaceutically acceptable salts thereof, as such, or combined with other compatible active principles, and/or with pharmaceutically acceptable carriers, diluents, solvents and/or excipients.

Said pharmaceutical compositions may be so formulated as to be administrable by oral way, by rectal way, by injection and topically; they can be e.g. in the solid form, as e.g. capsules, tablets, long-release tablets, single-dose bags, suppositories, ointments, salves, and in the liquid form, such as solutions, suspensions, or emulsions, ready-to-use or for extemporaneous preparation. All the above described pharmaceutical preparations may be so formulated as to contain diluents, carriers, solvents and/or excipients well known in the art, and may be prepared according to the methods well known in the art and widely described, e.g. in "Tecnologia Farmaceutica", Silvano Casadio - Ed. Cisalpino Goliardica, Milano 1972.

TABLE 2

Antihistaminic anti-$H_2$ activity, gastric secretion in rats, in vivo, induced by histamine.
Histamine perfused into vein 200 μg/kg/min at the flow rate of 0.1 ml/min.
Perfusion of stomach with 0.00025 N NaOH at the flow rate of 1 ml/min.

| Test | Dosage mg/kg i.p. | Weight $\overline{X}$ g | pH VARIATION FROM THE BEGINNING OF THE TREATMENT $\overline{X} \pm ES$ | | | | | | |
|---|---|---|---|---|---|---|---|---|---|
| | | | 0' | 5' | 10' | 15' | 20' | 25' | 30' |
| C | — | 461.8 ± 21.5 | 8.62 ± 0.08 | 6.33 ± 0.30 | 4.74 ± 0.39 | 3.70 ± 0.28 | 3.23 ± 0.18 | 3.15 ± 0.18 | 3.15 ± 0.21 |
| A | 50 | 432.2 ± 14.6 | 8.68 ± 0.11 | 7.21 ± 0.26 | 5.85 ± 0.33 | 4.62 ± 0.59 | 4.43 ± 0.18 | 4.39 ± 0.15 | 4.27 ± 0.08 |
| B | 50 | 441.2 ± 15.5 | 8.80 ± 0.04 | 6.12 ± 0.21 | 4.06 ± 0.44 | 4.06 ± 0.25 | 4.28 ± 0.22 | 4.48 ± 0.20 | 4.67 ± 0.14 |

| Test | Dosage mg/kg i.p. | pH VARIATION FROM THE BEGINNING OF THE TREATMENT $\overline{X} \pm ES$ | | | | | | Area mm² $\overline{X} \pm ES$ | % Δ |
|---|---|---|---|---|---|---|---|---|---|
| | | 35' | 40' | 45' | 50' | 55' | 60' | | |
| C | — | 3.06 ± 0.23 | 2.91 ± 0.22 | 2.87 ± 0.24 | 2.87 ± 0.24 | 2.80 ± 0.25 | 2.77 ± 0.24 | 184.93 ± 8.21 | — |
| A | 50 | 4.06 ± 0.23 | 4.05 ± 0.22 | 3.97 ± 0.23 | 3.92 ± 0.21 | 3.99 ± 0.25 | 3.95 ± 0.27 | 245.67* ± 10.41 | 32.84 |
| B | 50 | 4.89 ± 0.13 | 5.16 ± 0.04 | 5.33 ± 0.10 | 5.40 ± 0.10 | 5.57 ± 0.14 | 5.69 ± 0.20 | 269.02** ± 6.41 | 45.47 |

C = Control
A = treatment with methylpiperazino-ranitidine
B = treatment with ranitidine
For each one of the 3 tests 5 animals were used
% Δ = percent increase relatively to the control
Statistic analysis: Student's "t" test *p ≦ 0.01 **p ≦ 0.01

The new compound, being the object of the present invention, can be administered both as such and as pharmaceutical acceptable salts thereof, in amounts of from 0.2 to 50 mg/kg per day, and preferably, of from 0.5 to 20 mg/kg per day, usefully as subdivided dosages such as e.g. from twice to four times a day in dosage units containing e.g. 10, 20, 30, 50, 100, 200, 250, 500 mg of active principle.

The compound of formula (I) and its pharmaceutically acceptable salts can be prepared, and this is a further object of the present invention, by reacting 2-[[[5-[(dimethylamino)-methyl]-2-furanyl]-methyl]-thio]-ethylmethyl-sulphide, of formula (III)

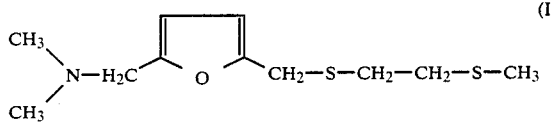
(III)

with the compound of formula (II)

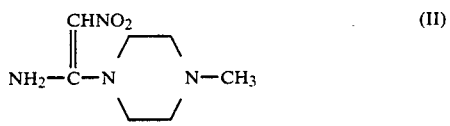
(II)

at the temperature of 80° C., isolating the compound of formula (I) obtained and optionally salifying the compound obtained. Advantageously, an excess of the compound of formula (II) is used, and the reaction is usefully carried out in three hours.

The compound of formula (II) can be obtained, and this too is an object of the present invention, by reacting 1,1-bis-(methylthio)-2-nitroethene of formula (IV)

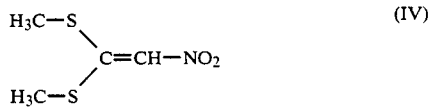
(IV)

with 4-methylpiperazine and then with ammonia.

Such a reaction can be usefully carried out in organic solvents, advantageously in tetrachloroethane. The product obtained can be purified by being passed over a silica gel column and subsequent crystallization.

The compound of formula (III) can be obtained on the contrary according to the process disclosed in laid open Italian Patent Application No. 19473A/82 filed in the same Applicant's name.

The compound of formula (I) obtained can be easily isolated according to the technologies well known to those skilled in the art, e.g. by crystallization from solvents; such solvents are suitably constituted by a water-ethanol mixture.

Also the optional salification may be carried out according the the techniques well known in the art, e.g. by means of the addition of the suitable acid.

The following Examples illustrate some embodiments of the present invention, without however limiting it in any way.

EXAMPLE 1

1-N-[2-[[5-[(dimethylamino)-methyl]-furfuryl]-thio]-ethyl]-amino-1-[4-methylpiperazino]-2-nitroethene An amount of 24.54 g of 2-[[5-[(dimethylamino)-methyl]-furfuryl]-thio]-ethylmethyl-sulphide is reacted with 43 g of 1-amino-1-[4-methylpiperazino]-2-nitroethene at 80° C. over three hours.

The mixture is cooled and is collected with diethyl ether.

The reaction mass is filtered, the precipitate is dissolved in ethyl alcohol and is precipitated again with water. The product is crystallized from a water - ethyl alcohol mixture. The spectrophotometric analyses confirm its structure. Elemental analysis $C_{17}H_{29}N_5 SO_3$. Molecular weight 383.46.

| | C | H | N | S | O |
|---|---|---|---|---|---|
| Calculated | 53.24% | 7.62% | 18.25% | 8.37% | 12.52% |
| Found | 53.25% | 7.63% | 18.3% | 8.4% | 12.6% |

EXAMPLE 2

1-Amino-1-[4-methylpiperazino]-2-nitroethene

An amount of 16.5 g of 1,1-bis-(methylthio)-2-nitroethene is dissolved at high temperature in 100 ml of tetrachloroethane, equimolar amounts of methyl-piperazine are added, the mixture is refluxed over 2 hours; the mass is cooled and anhydrous gaseous ammonia is added to it up to saturation.

The mass is stirred for two hours. The solvent is evaporated in vacuo and the product obtained is purified over a silica gel chromatographic column; the elution is carried out with petroleum ether and then with dichloroethane.

The product which is separated is crystallized from diethyl ether.

Although the invention has been disclosed in detail with reference to some specific embodiments thereof, it is clear to those skilled in the art that some changes and modifications may be done always within the limits of the present invention.

Therapeutical Indications

Methylpiperazino-ranitidine is indicated in all conditions under which a controlled reduction of stomach acid secretion is required, to the purpose of relieving the pain and/or of achieving the recovery. Such conditions include duodenal ulcer, benign gastric ulcer, relapsing ulcer, post-operative ulcer, oesophagitis, Zollinger-Ellison syndrome.

Methylpiperazino-ranitidine is also indicated under such conditions as hypertrophic chronic gastritis or under other conditions under which the presence of gastric acidity is harmful.

I claim:

1. Compound of formula:

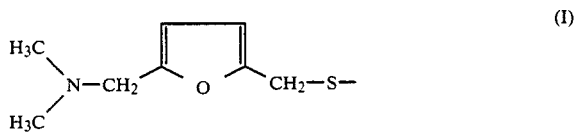
(I)

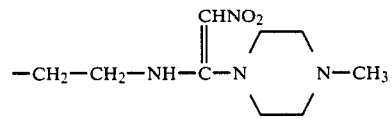

1-N—[2-[[5-[(dimethylamino)-methyl]-furfuryl]-thio]-ethyl]-amino-1-]4-methyl-piperazino]-2-nitroethene, and its pharmaceutically acceptable salts.

2. Compound according to claim 1, characterized in that said pharmaceutically acceptable salt is the salt with hydrochloric, hydrobromic, hydriodic, phosphoric, sulphuric, maleic, malic, acetic, citric, oxalic, succinic, benzoic, tartaric, fumaric, mandelic, ascorbic, methylsulphonic or ethylsulphonic acid.

3. A pharmaceutical composition comprising a therapeutically efficacious amount of the compound according to claim 1 and a pharmaceutically acceptable carrier, diluent, solvent, or excipient.

4. Composition according to claim 3, characterized in that it is suitable to be administered by oral way, by injection, by rectal way or topically.

5. Composition according to claim 3, characterized in that it is in the form of a tablet.

6. Composition according to claim 5, characterized in that it is in the form of a tablet with characteristics of long - and progressive-release of the active principle.

7. Composition according to claim 5, characterized in that each tablet contains from 20 to 500 mg of active principle.

8. Composition according to claim 3 characterized in that it is in the form of a single-dose bag, ready-to-use or extemporaneous syrup or emulsion.

9. Composition according to claim 3, characterized in that it is in the form of an ointment, a cream or a powder for topic application.

10. Composition according to claim 9 characterized in that the content of active principle can be of from 0.5 to 10%.

* * * * *